(12) United States Patent
Hoornaert

(10) Patent No.: US 7,868,007 B2
(45) Date of Patent: Jan. 11, 2011

(54) TRIAZOLOPYRIDINE CARBOXAMIDE DERIVATIVES, PREPARATION THEREOF AND THERAPEUTIC USE THEREOF

(75) Inventor: Christian Hoornaert, Paris (FR)

(73) Assignee: sanofi-aventis, Paris (FR)

( * ) Notice: Subject to any disclaimer, the term of this patent is extended or adjusted under 35 U.S.C. 154(b) by 0 days.

(21) Appl. No.: 12/573,961

(22) Filed: Oct. 6, 2009

(65) Prior Publication Data
US 2010/0035893 A1 Feb. 11, 2010

Related U.S. Application Data

(63) Continuation of application No. PCT/FR2008/000535, filed on Apr. 16, 2008.

(30) Foreign Application Priority Data

Apr. 18, 2007 (FR) .................................. 07 02807

(51) Int. Cl.
*A61K 31/4353* (2006.01)
*A61K 31/496* (2006.01)
*C07D 471/04* (2006.01)
(52) U.S. Cl. .................................. 514/253.04; 544/362
(58) Field of Classification Search ........................ None
See application file for complete search history.

(56) References Cited

FOREIGN PATENT DOCUMENTS

| WO | WO 02/055083 | 7/2002 |
| WO | WO 2004/035550 | 4/2004 |
| WO | WO 2005/073199 | 8/2005 |
| WO | WO 2006/138657 | 12/2006 |
| WO | WO 2007/045392 | 4/2007 |

OTHER PUBLICATIONS

Magrioti et al. Bioorganic & Medicinal Chemistry Letters, vol. 18, p. 5424-5427 (2008).*
Dinh, T. P., et. al., Brain Monoglyceride Lipase Participating in Endocannabinoid Inactivation, PNAS, (2002), vol. 99, No. 16, pp. 10819-10824.
Dinh, T. P., et. al., RNA Interference Suggests a Primary Role for Monoacylglycerol Lipase in the Degradation of the Endocannabinoid 2-Arachidonoylglycerol, Molecular Pharmacology, (2004), vol. 66, No. 5, pp. 1250-1264.
Karlsson, M., et. al., cDNA Cloning, Tissue Distribution, and Identification of the Catalytic Triad of Monoglyceride Lipase, The Journal of Biological Chemistry, vol. 272, No. 43, pp. 27218-27223, (1997).
Kondo, S., et. al., 2-Arachidoncylglycerol, an Endogenous Cannabinoid Receptor Agonist: Identifications as One of the Major Species of Monoacylglycerois in Various Rat Tissues, and Evidence for its Generation Through Ca2+-Dependent and -Independent Mechanisms, FEBS Letters, vol. 429, (1998), pp. 152-156.
Rice, K. D., et. al., Dibasic Inhibitors of Human Mast Cell Tryptase. Part 1: Synthesis and Optimization of a Novel Class of Inhibitors, Bioorganic & Medicinal Chemistry Letters, vol. 10, (2000), pp. 2357-2360.
Saario, S. M., et. al., Monoglyceride Lipase-Like Enzymatic Activity is Responsible for Hydrolysis of 2-Arachidonoylglycerol in Rat Cerebellar Membranes, Biochemical Pharmacology, vol. 67, (2004), pp. 1381-1387.
Savinainen, J. R. , et. al. , Despite Substantial Degradation, 2-Arachidonoylglycerol is a Potent Full Efficacy Agonist Mediating CB1 Receptor-Dependent G-Protein Activation in Rat Cerebellar Membranes, British Journal of Pharmacology, (2001), vol. 134, pp. 664-672.
Sugiura, T., et. al., Biochemistry, Pharmacology and Physiology of 2-Arachidonoylglycerol, an Endogenous Cannabinoid Receptor Ligand , Progress in Lipid Research, vol. 45, (2006) pp. 405-446.
Sugiura, T., et. al., Evidence That 2-Arachidonoylglycerol but Not N-Palmitoylethanolamine or Anandamide is the Physiological Ligand for the Cannabinoid CB2 Receptor, The Journal of Biological Chemistry, vol. 275, No. 1, pp. 605-612, (2000).
Sugiura, T., et. al., Evidence That the Cannabinoid CB1 Receptor Is a 2-Arachidonoylglycerol Receptor, The Journal of Biological Chemistry, vol. 274, No. 5, pp. 2794-2801, (1999).
Vaughn, J. R., et. al., Triazolo and Imidiazopyridines, J. Am. Chem. Soc., (1949), pp. 1885-1887.
Fowler, C. J., et. al., Ibuprofen Inhibits Rat Brain Deamidation of Anandamide at Phamacologically Relevant Concentrations. Mode of Inhibition and Structure-Activity Relationship, The Journal of Pharmacology and Experimental Therapeutics, vol. 283, No. 2, pp. 729-734, (1997).
Omeir, R. L., et. al., Arachidonoyl Ethanolamide-[1,2-14c] as a Substrate for Anandamide Amidase, Life Sciences, vol. 56, No. 23/24, pp. 1999-2005, (1995).
Ueda, N., et. al., The Fatty Acid Amide Hydrolase (FAAH), Chemistry and Physics of Lipids, vol. 108, (2000), pp. 107-121.

* cited by examiner

*Primary Examiner*—Emily Bernhardt
(74) *Attorney, Agent, or Firm*—Balaram Gupta; Kelly L. Bender

(57) ABSTRACT

The invention relates to the triazolopyridine carboxamide derivatives of general formula (I):

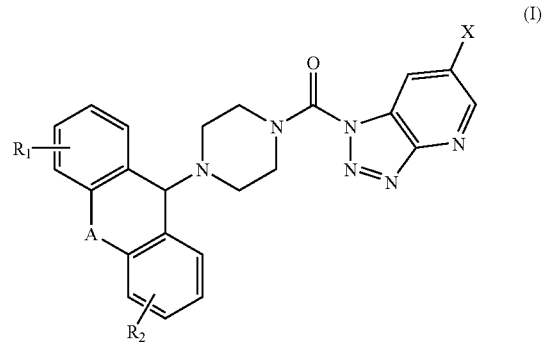

Wherein X, A, $R_1$ and $R_2$ are as defined herein. The invention further relates to preparation methods and therapeutic use thereof.

15 Claims, No Drawings

TRIAZOLOPYRIDINE CARBOXAMIDE DERIVATIVES, PREPARATION THEREOF AND THERAPEUTIC USE THEREOF

This application is a continuation of International application No. PCT/FR2008/000,535, filed Apr. 16, 2008, which is incorporated herein by reference in its entirety; which claims the benefit of priority of French Patent Application No. 07/02, 807, filed Apr. 18, 2007.

The present invention relates to triazolopyridine carboxamide derivatives, to the preparation thereof and to the therapeutic use thereof.

The subject of the present invention is the compounds corresponding to formula (I)

(I)

in which:

X is a hydrogen atom, a halogen atom, or a $(C_1-C_6)$alkyl, $(C_1-C_6)$alkoxy, halo$(C_1-C_6)$alkyl, $S(O)_m R''$, hydroxyl or cyano group, A is absent or else is a bond, an oxygen atom, a sulfur atom, an NR, C(O)NR' or $SO_2NR'$ group, a $(C_1-C_2)$alkylene group or a $(C_2)$alkenyl group, $R_1$ and $R_2$ are, independently of one another, one or more groups selected from a hydrogen atom, a $(C_1-C_6)$alkyl group, a $(C_1-C_6)$alkoxy group, a $(C_3-C_7)$cycloalkyl group, a $(C_3-C_7)$cycloalkyl$(C_1-C_6)$alkyl group, a $(C_3-C_7)$cycloalkyl$(C_1-C_6)$alkoxy group, a halogen atom, a cyano group, a C(O)R', C(O)OR', C(O)$NR_{10}R_{20}$ or $NO_2$ group, or an $NR_{10}R_{20}$ or $NR_{10}C(O)$—$R_{20}$ group, the $(C_1-C_6)$alkyl and $(C_1-C_6)$alkoxy groups being optionally substituted with one or more atoms or groups selected, independently of one another, from halogen atoms and hydroxyl, amino or $NR_{10}R_{20}$ groups, R is a group selected from a hydrogen atom, and a $(C_1-C_6)$alkyl, $(C_3-C_7)$cycloalkyl, $(C_3-C_7)$cycloalkyl$(C_1-C_6)$alkyl, C(O)R', $SO_2R''$, $CO_2R''$ or C(O)$NR_{10}R_{20}$ group, R' is a group selected from a hydrogen atom, a $(C_1-C_6)$alkyl group, a $(C_3-C_7)$cycloalkyl group and a $(C_3-C_7)$cycloalkyl$(C_1-C_6)$alkyl group, R'' is a group selected from a $(C_1-C_6)$alkyl group, a $(C_3-C_7)$cycloalkyl group and a $(C_3-C_7)$cycloalkyl$(C_1-C_6)$alkyl group, $R_{10}$ and $R_{20}$ are, independently of one another, one or more groups selected from a hydrogen atom, a $(C_1-C_6)$alkyl group, a $(C_3-C_7)$cycloalkyl group and a $(C_3-C_7)$cycloalkyl$(C_1-C_6)$alkyl group, or else $R_{10}$ and $R_{20}$ can form a saturated or partially unsaturated ring containing from 5 to 7 carbon atoms and optionally containing a heteroatom chosen from O, N or $S(O)_m$, m represents 0, 1 or 2.

The compounds of formula (I) can contain one or more asymmetrical carbon atoms. They can therefore exist in the form of enantiomers or of diastereoisomers. These enantiomers and diastereoisomers, and also mixtures thereof, including racemic mixtures, are part of the invention.

The compounds of formula (I) can exist in the form of bases or of addition salts with acids. Such addition salts are part of the invention.

These salts can be prepared with pharmaceutically acceptable acids, but the salts of other acids that are useful, for example, for purifying or isolating compounds of formula (I) are also part of the invention.

The compounds of formula (I) can also exist in the form of hydrates or of solvates, i.e. in the form of associations or of combinations with one or more molecules of water or with a solvent. Such hydrates and solvates are also part of the invention.

In the context of the present invention:

$C_{t-z}$, where t and z can take the values of 1 to 7, is intended to mean a carbon chain or ring that can have from t to z carbon atoms; for example, $C_{1-3}$ can characterize a carbon chain containing from 1 to 3 carbon atoms;

a halogen atom is intended to mean: a fluorine, a chlorine, a bromine or an iodine;

an alkyl group is intended to mean: a linear or branched, saturated aliphatic group. By way of examples, mention may be made of methyl, ethyl, propyl, isopropyl, butyl, isobutyl, tert-butyl, pentyl, etc, groups;

a cycloalkyl group is intended to mean: a saturated cyclic aliphatic group. By way of examples, mention may be made of cyclopropyl, cyclobutyl, cyclopentyl, cyclohexyl, etc, groups;

an alkylene group is intended to mean: a linear or branched, saturated divalent aliphatic group. By way of example, a $C_{1-3}$-alkylene group is a linear or branched, divalent carbon chain containing from 1 to 3 carbon atoms, such as a methylenyl (—$CH_2$—), an ethylenyl (—$CH_2CH_2$—), a 1-methylethylenyl (—CH($CH_3$) $CH_2$—), a propylenyl (—$CH_2CH_2CH_2$—), etc;

an alkenyl group is intended to mean: a linear or branched, monounsaturated or polyunsaturated aliphatic group comprising, for example, one or two ethylenic unsaturations; by way of example, a $(C_2)$alkenyl group is a carbon chain containing 2 carbon atoms and one ethylenic unsaturation, such as an ethenyl (—CH=CH—);

an alkoxy group is intended to mean: an —O-alkyl radical where the alkyl group is as defined above;

a haloalkyl group is intended to mean: an alkyl group in which one or more hydrogen atoms have been substituted with a halogen atom. By way of examples, mention may be made of —$CF_3$ and —$CH_2CF_3$ groups;

the sulfur atoms may be present in the oxidized state (sulfoxide, sulfone).

In the various groups as defined below, the groups $R_1$, $R_2$, R and R', when they are not defined, have the same meanings as those mentioned above.

Among the compounds of formula (I) which are subjects of the invention, a first group of compounds comprises the compounds for which:

X is a hydrogen or halogen atom,

A is absent or else is a bond, an oxygen atom, a sulfur atom, an NR, C(O)NR' or $SO_2NR'$ group, a $(C_1-C_2)$alkylene group or a $(C_2)$alkenyl group.

Among the compounds of formula (I) which are subjects of the invention, a second group of compounds comprises the compounds of formula (I) for which:
X is a hydrogen or halogen atom,
A is absent or else is a bond or a ($C_1$-$C_2$)alkylene group,
$R_1$ and $R_2$ are, independently of one another, one or more groups selected from a hydrogen atom, a halogen atom, a cyano group or an alkoxy group.

Among the compounds of formula (I) which are subjects of the invention, a third group of compounds comprises the compounds of formula (I) for which:
X is a hydrogen or halogen atom,
A is absent or else is a bond or an ethylene group,
$R_1$ and $R_2$ are, independently of one another, one or more groups selected from a hydrogen or halogen atom.

Among the compounds of formula (I) which are subjects of the invention, a fourth group of compounds comprises the compounds of formula (I) for which:
X is a hydrogen or chlorine atom,
A is absent or else is a bond or an ethylene group,
$R_1$ and $R_2$ are, independently of one another, one or more groups selected from a hydrogen atom, a fluorine atom or a chlorine atom.

The combinations of groups one to four as defined above are also part of the invention.

Among the compounds of formula (I) which are subjects of the invention, mention may in particular be made of the following compounds:
(4-benzhydrylpiperazin-1-yl)[1,2,3]triazolo[4,5-b]pyridin-1-ylmethanone;
(4-benzhydrylpiperazin-1-yl)(6-chloro[1,2,3]triazolo[4,5-b]pyridin-1-yl)methanone;
{4-[bis(4-fluorophenyl)methyl]piperazin-1-yl}[1,2,3]triazolo[4,5-b]pyridin-1-ylmethanone;
{4-[bis(4-chlorophenyl)methyl]piperazin-1-yl}[1,2,3]triazolo[4,5-b]pyridin-1-ylmethanone;
{4-[bis(4-fluorophenyl)methyl]piperazin-1-yl}(6-chloro[1,2,3]triazolo[4,5-b]pyridin-1-yl)-methanone;
{4-[bis(4-chlorophenyl)methyl]piperazin-1-yl}(6-chloro[1,2,3]triazolo[4,5-b]pyridin-1-yl)-methanone;
[4-(10,11-dihydro-5H-dibenzo[a,d]cyclohepten-5-yl)piperazin-1-yl][1,2,3]triazolo[4,5-b]-pyridin-1-ylmethanone;
[4-(9H-fluoren-9-yl)piperazin-1-yl][1,2,3]triazolo[4,5-b]pyridin-1-ylmethanone.

In the subsequent text, the term "protective group Pg" is intended to mean a group which makes it possible, firstly, to protect a reactive function such as a hydroxyl or amine during a synthesis and, secondly, to regenerate the intact reactive function at the end of synthesis. Examples of protective groups and also protection and deprotection methods are given in "Protective Groups in Organic Synthesis", Greene et al., 2nd Edition (John Wiley & Sons, Inc., New York), 1991.

In the subsequent text, the term "leaving group" is intended to mean a group that can be readily cleaved from a molecule by breaking a heterolytic bond, with the departure of a pair of electrons. This group can thus be readily replaced with another group during a substitution reaction, for example. Such leaving groups are, for example, halogens or an activated hydroxyl group such as a methanesulfonate, benzenesulfonate, p-toluenesulfonate, triflate, acetate, etc. Examples of leaving groups and also references for the preparation thereof are given in "Advances in Organic Chemistry", J. March, 3rd Edition, Wiley Interscience, 1985, p. 310-316.

In accordance with the invention, the compounds of formula (I) can be prepared according to the process which follows.

A first method (scheme 1) consists in reacting a triazolopyridine derivative of formula (II) in which X is as defined above, with a carbamoyl chloride of formula (III) in which $R_1$, $R_2$ and A are as defined above, in a solvent such as tetrahydrofuran, in the presence of a base such as diisopropylethylamine and of a catalyst such as 4-dimethylaminopyridine.

Scheme 1

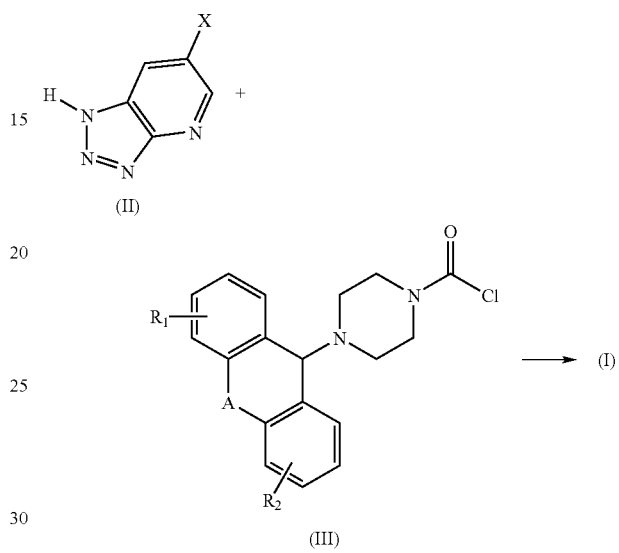

A second method (scheme 2) consists in reacting a triazolopyridine derivative of formula (IV) in which X is as defined above, with a derivative of formula (V) in which $R_1$, $R_2$ and A are as defined above and L is a leaving group, in a solvent such as acetonitrile and in the presence of a base such as diisopropylethylamine.

Scheme 2

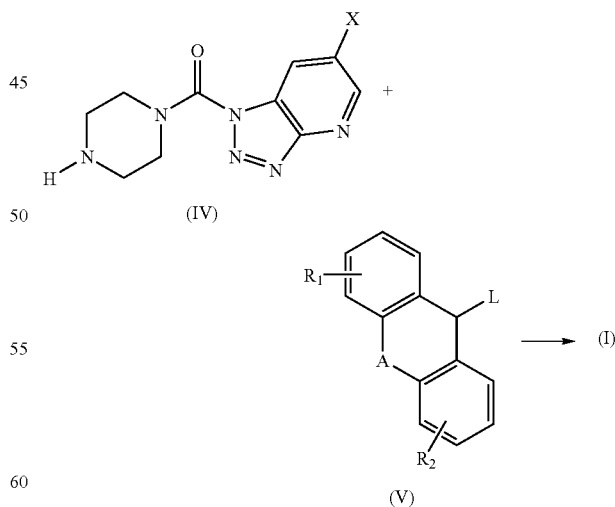

The compounds of formulae (II), (III), (IV) and (V), when the method for preparing them is not described above, are commercially available or described in the literature, or else can be prepared according to methods which are described therein or which are known to those skilled in the art.

According to another of its aspects, a subject of the invention is also the compounds of formula (IV), in which X is as defined above, in their base or salt form. These compounds are of use as intermediates for the synthesis of the compounds of formula (I).

The examples which follow illustrate the preparation of some compounds of the invention. These examples are not limiting and merely illustrate the invention. The microanalyses, the IR and NMR spectra and/or the LC-MS analyses confirm the structures and the purities of the compounds obtained. The numbers of the compounds exemplified refer to those given in the table hereinafter, which illustrates the chemical structures and the physical properties of some compounds according to the invention.

EXAMPLE 1

(4-Benzhydrylpiperazin-1-yl)[1,2,3]triazolo[4,5-b]pyridin-1-ylmethanone

1.1. 4-Benzhydrylpiperazine-1-carbonyl chloride

A solution of 2.522 g (10 mmol) of 1-benzhydrylpiperazine and of 1.62 ml (20 mmol) of pyridine in 15 ml of dichloromethane is added, dropwise, to a solution of 1.187 g (4 mmol) of triphosgene in 10 ml of dichloromethane, cooled to −5° C. under an argon atmosphere. Stirring is continued at −5° C. for 15 minutes and then at ambient temperature for 3 hours. 50 ml of dichloromethane and 50 ml of water are subsequently added. The mixture is separated by settling out and the organic phase is washed with 2×25 ml of water and then 25 ml of a saturated aqueous solution of sodium chloride. The product is dried over sodium sulfate and evaporated under vacuum, so as to obtain 2.72 g of product in the form of a gum, used as it is in the following step.

1.2. (4-Benzhydrylpiperazin-1-yl)[1,2,3]triazolo[4,5-b]pyridin-1-ylmethanone 0.62 ml (3.75 mmol) of diisopropylethylamine is added to a suspension of 0.865 g (2.75 mmol) of 4-benzhydrylpiperazine-1-carbonyl chloride obtained in step 1.1., of 0.300 g (2.50 mmol) of 1H-[1,2,3]triazolo[4,5-b]pyridine and of 0.015 g (0.12 mmol) of 4-dimethylaminopyridine in 5 ml of tetrahydrofuran. The mixture is stirred at ambient temperature for 4 hours and then 60 ml of ethyl acetate and 15 ml of water are added. The organic phase is separated by settling out and washed with 2×15 ml of water and then 15 ml of a saturated aqueous solution of sodium chloride. The product is dried over sodium sulfate and evaporated under vacuum. The product is purified by silica gel chromatography, elution being carried out with a 25:75, then 30:70, 35:65 and 40:60 mixtures of ethyl acetate and cyclohexane. The product is subsequently recrystallized from isopropanol, so as to obtain 0.63 g (1.58 mmol) of product in the form of white crystals.

Melting point (° C.): 146-148 (decomposition)
LC-MS (m/z): 399 (MH+)
IR (KBr, cm$^{-1}$): 1697
$^1$H-NMR (CDCl$_3$, δ ppm): 8.80 (dd, 1H), 8.40 (dd, 1H), 7.55 (dd, 1H), 7.45-7.15 (m, 10H), 4.35 (s, 1H), 4.00 (m, 4H), 2.60 (m, 4H).

EXAMPLE 2

(4-Benzhydrylpiperazin-1-yl)(6-chloro[1,2,3]triazolo[4,5-b]pyridin-1-yl)methanone The process is carried out as described in Example 1, using 0.651 g (2.07 mmol) of 4-benzhydrylpiperazine-1-carbonyl chloride and 0.278 g (1.80 mmol) of 6-chloro-1H-[1,2,3]triazolo[4,5-b]pyridine (J. Am. Chem. Soc. 1949, 1885). The product is recrystallized from a mixture of 2-butanone and diisopropyl ether, so as to obtain 0.46 g (1.06 mmol) of product in the form of white crystals.

Melting point (° C.): 173-175 (decomposition)
LC-MS (m/z): 455 (MNa+), 471 (MK+)
IR (KBr, cm$^{-1}$): 1706
$^1$H-NMR (CDCl$_3$, δ ppm): 8.75 (s, 1H), 8.30 (s, 1H), 7.45 (m, 4H), 7.35-7.20 (m, 6H), 4.35 (s, 1H), 4.00 (m, 4H), 2.65 (m, 4H).

EXAMPLE 3

{4-[Bis(4-fluorophenyl)methyl]piperazin-1-yl}[1,2,3]triazolo[4,5-b]pyridin-1-ylmethanone The process is carried out according to Example 1, using 0.757 g (2.16 mmol) of 4-[bis(4-fluorophenyl)methyl]piperazine-1-carbonyl chloride (obtained according to Example 1.1) and 0.216 g (1.80 mmol) of 1H-[1,2,3]triazolo[4,5-b]pyridine. The product is recrystallized from isopropanol, so as to obtain 0.50 g (1.15 mmol) of product in the form of white crystals.

Melting point (° C.): 151-153 (decomposition)
LC-MS (m/z): 435 (MH+)
IR (KBr, cm$^{-1}$): 1712
$^1$H-NMR (CDCl$_3$, δ ppm): 8.85 (d, 1H), 8.40 (d, 1H), 7.55 (dd, 1H), 7.40 (m, 4H), 7.05 (m, 4H), 4.40 (s, 1H), 4.00 (m, 4H), 2.60 (m, 4H).

EXAMPLE 4

{4-[Bis(4-chlorophenyl)methyl]piperazin-1-yl}[1,2,3]triazolo[4,5-b]pyridin-1-ylmethanone The process is carried out according to Example 1, using 0.882 g (2.30 mmol) of 4-[bis(4-chlorophenyl)methyl]piperazine-1-carbonyl chloride (obtained according to Example 1.1) and 0.240 g (2 mmol) of 1H-[1,2,3]triazolo[4,5-b]pyridine. The product is recrystallized from a mixture of 2-butanone and diisopropyl ether, so as to obtain 0.57 g (1.22 mmol) of product in the form of white crystals.

Melting point (° C.): 163-165 (decomposition)
LC-MS (m/z): 467 (MH+)
IR (KBr, cm$^{-1}$): 1715
$^1$H-NMR (CDCl$_3$, δ ppm): 8.70 (d, 1H), 8.30 (d, 1H), 7.45 (dd, 1H), 7.30-7.15 (m, 8H), 4.25 (s, 1H), 3.90 (m, 4H), 2.50 (m, 4H).

EXAMPLE 5

{4-[Bis(4-fluorophenyl)methyl]piperazin-1-yl}(6-chloro[1,2,3]triazolo[4,5-b]pyridin-1-yl)-methanone The process is carried out according to Example 1, using 0.757 g (2.16 mmol) of 4-[bis(4-fluorophenyl)methyl]piperazine-1-carbonyl chloride and 0.278 g (1.80 mmol) of 6-chloro-1H-[1,2,3]triazolo[4,5-b]pyridine. The product is recrystallized from isopropanol, so as to obtain 0.60 g (1.28 mmol) of product in the form of white crystals.

Melting point (° C.): 167-169 (decomposition)
LC-MS (m/z): 469 (MH+)
IR (KBr, cm$^{-1}$): 1704
$^1$H-NMR (CDCl$_3$, δ ppm): 8.75 (s, 1H), 8.40 (s, 1H), 7.40 (m, 4H), 7.05 (m, 4H), 4.35 (s, 1H), 4.00 (m, 4H), 2.60 (m, 4H).

EXAMPLE 6

{4-[Bis(4-chlorophenyl)methyl]piperazin-1-yl}(6-chloro[1,2,3]triazolo[4,5-b]pyridin-1-yl)-methanone The process is carried out according to Example 1, using 0.926 g (2.41 mmol) of 4-[bis(4-chlorophenyl)methyl]piperazine-1-carbonyl chloride and 0.324 g (2.10 mmol) of 6-chloro-1H-[1,2,3]triazolo[4,5-b]pyridine. The product is recrystallized from a mixture of 2-butanone and diisopropyl ether, so as to obtain 0.71 g (1.41 mmol) of product in the form of white crystals.

Melting point (° C.): 172-174 (decomposition)
IR (KBr, cm$^{-1}$): 1702
$^1$H-NMR (d$_6$-DMSO, δ ppm): 8.85 (s, 1H), 8.50 (s, 1H), 7.45 (d, 4H), 7.40 (d, 4H), 4.55 (s, 1H), 3.80 (m, 4H), 2.45 (m, 4H).

EXAMPLE 7

[4-(10,11-Dihydro-5H-dibenzo[a,d]cyclohepten-5-yl)piperazin-1-yl][1,2,3]triazolo[4,5-b]-pyridin-1-ylmethanone The process is carried out according to Example 1, using 0.790 g (2.32 mmol) of 4-(10,11-dihydro-5H-dibenzo[a,d]cyclohepten-5-yl)piperazine-1-carbonyl chloride (obtained according to Example 1.1) and 0.278 g (2.32 mmol) of 1H-[1,2,3]triazolo[4,5-b]pyridine. The product is recrystallized from ethyl acetate, so as to obtain 0.26 g (0.61 mmol) of product in the form of white crystals.

Melting point (° C.): 190-194 (decomposition)
LC-MS (m/z): 447 (MNa+), 463 (MK+), 871 (MMNa+)
IR (KBr, cm$^{-1}$): 1707
$^1$H-NMR (CDCl$_3$, δ ppm): 8.80 (d, 1H), 8.35 (d, 1H), 7.55 (dd, 1H), 7.25-7.05 (m, 8H), 4.15-3.85 (m, 7H), 2.95-2.80 (m, 2H), 2.55 (m, 4H).

EXAMPLE 8

[4-(9H-Fluoren-9-yl)piperazin-1-yl][1,2,3]triazolo[4,5-b]pyridin-1-ylmethanone

8.1. tert-Butyl 4-([1,2,3]triazolo[4,5-b]pyridine-1-carbonyl)piperazine-1-carboxylate 1.39 ml (8.40 mmol) of diisopropylethylamine are added to a suspension of 0.840 g (7 mmol) of 1H-[1,2,3]triazolo[4,5-b]pyridine, of 1.741 g (7 mmol) of tert-butyl 4-chlorocarbonylpiperazine-1-carboxylate (Bioorg. Med. Chem. Lett. 2000, 10, 2357) and of 0.042 g (0.35 mmol) of 4-dimethylaminopyridine in 14 ml of tetrahydrofuran. The mixture is stirred at ambient temperature for 4 hours and then 80 ml of ethyl acetate and 20 ml of water are added. The organic phase is separated by settling out and is then washed with 3×20 ml of water and 20 ml of a saturated aqueous solution of sodium chloride. The product is dried over sodium sulfate and evaporated to dryness. The residue is recrystallized from isopropanol, so as to obtain 1.70 g (5.1 mmol) of product in the form of white crystals.

Melting point (° C.): 155-157 (decomposition)

8.2. Piperazin-1-yl[1,2,3]triazolo[4,5-b]pyridin-1-ylmethanone dihydrochloride 1.8 ml of a 5N solution of hydrochloric acid (9 mmol) in isopropanol are added to a solution of 0.498 g (1.50 mmol) of tert-butyl 4-([1,2,3]triazolo[4,5-b]pyridine-1-carbonyl)piperazine-1-carboxylate prepared in step 8.1., in 7.5 ml of dichloromethane. Stirring is continued overnight at ambient temperature. The solid form is filtered off and is washed with 3 ml of dichloromethane and with 2×6 ml of diisopropyl ether, and then dried under vacuum in the presence of phosphorus pentoxide, so as to obtain 0.46 g (1.5 mmol) of product in the form of white powder.

Melting point (° C.): 160 (decomposition)
LC-MS (m/z): 233 (MH+)
IR (KBr, cm$^{-1}$): 1714
$^1$H-NMR (d$_6$-DMSO, δ ppm): 9.60 (m, 2H), 8.80 (d, 1H), 8.40 (d, 1H), 7.75 (dd, 1H), 4.05 (m, 4H), 3.25 (m, 4H)

8.3. [4-(9H-Fluoren-9-yl)piperazin-1-yl][1,2,3]triazolo[4,5-b]pyridin-1-ylmethanone 0.83 ml (5 mmol) of diisopropylethylamine is added to a suspension of 0.381 g (1.25 mmol) of piperazin-1-yl[1,2,3]triazolo[4,5-b]pyridin-1-ylmethanone dihydrochloride, prepared in step 8.2., and of 0.337 g (1.38 mmol) of 9-bromo-9H-fluorene in 4 ml of acetonitrile. The solution is stirred overnight at ambient temperature and is then evaporated. The residue is taken up in a mixture of 40 ml of ethyl acetate and 10 ml of water. The mixture is separated by settling out and the organic phase is washed with 2×10 ml of water and then with 10 ml of a saturated aqueous solution of sodium chloride. The product is dried over sodium sulfate and evaporated under vacuum. The product is purified by silica gel chromatography, elution being carried out with a 40:60 then 50:50 mixture of ethyl acetate and cyclohexane, and then recrystallized from isopropanol, so as to obtain 0.40 g (1.01 mol) of product in the form of white crystals.

Melting point (° C.): 170-172 (decomposition)
LC-MS (m/z): 397 (MH+), 815 (MMNa+)
IR (KBr, cm$^{-1}$): 1723
$^1$H-NMR (CDCl$_3$, δ ppm): 8.80 (dd, 1H), 8.35 (dd, 1H), 7.75-7.65 (m, 4H), 7.55 (dd, 1H), 7.45-7.25 (m, 4H), 4.95 (s, 1H), 3.95 (m, 4H), 2.85 (m, 4H).

The table which follows illustrates the chemical structures and the physical properties of some examples of compounds according to the invention. In this table:

Mp (° C.) is the melting point of the compound in degrees Celsius;

in column "A", "-" signifies that A is absent;

in the "salt" column, "-" represents a compound in the form of a free base, whereas "HCl" represents a compound in hydrochloride form.

The compounds described in this table were prepared according to the methods described above.

TABLE 1

(I)

[Structure: phenyl-A-phenyl system with R1 and R2 substituents, connected via CH to piperazine-N, which bears a carbonyl linked to a triazolopyridine with X substituent]

| No. | X  | A         | R1   | R2   | Salt | Mp (° C.) |
|-----|----|-----------|------|------|------|-----------|
| 1   | H  | —         | H    | H    | —    | 146-148   |
| 2   | Cl | —         | H    | H    | —    | 173-175   |
| 3   | H  | —         | 4-F  | 4-F  | —    | 151-153   |
| 4   | H  | —         | 4-Cl | 4-Cl | —    | 163-165   |
| 5   | Cl | —         | 4-F  | 4-F  | —    | 167-169   |
| 6   | Cl | —         | 4-Cl | 4-Cl | —    | 172-174   |
| 7   | H  | —CH₂CH₂—  | H    | H    | —    | 190-194   |
| 8   | H  | bond      | H    | H    | —    | 170-172   |

The compounds according to the invention surprisingly exhibit an inhibitory effect on the MGL (monoacyl glycerol lipase) enzyme. The MGL enzyme catalyses the hydrolysis of endogenous derivatives of monoglyceride esters of various fatty acids (FEBS Letters 1998, 429, 152-156) and in particular the hydrolysis of 2-arachidonoylglycerol (2-AG) and of 1(3)-arachidonoylglycerol (1(3)-AG) (J. Biol. Chem. 1987, 272 (48), 27218-27223; Proc. Natl. Acad. Sci. USA 2002, 99 (16), 10819-10824; Biochem. Pharmacol. 2004, 67, 1381-1387; Mol. Pharmacol. 2004, 66 (5), 1260-1264). The 2-AG and 1-(3)-AG derivatives in particular interact with cannabinoid receptors (J. Biol. Chem. 1999, 274 (5), 2794-2801; J. Biol. Chem. 2000, 275 (1), 605-612; British J. Pharmacol. 2001, 134, 664-672).

The compounds of the invention block this degradation pathway and increase the tissue levels of these derivatives, and in particular of 2-AG and/or of 1(3)-AG. In this respect, they can be used in the prevention and treatment of pathologies in which 2-AG and/or 1(3)-AG, in particular, and/or any other substrate metabolized by the MGL enzyme, are involved (Progress Lipid Research 2006, 45, 405-446).

The compounds according to the invention have been the subject of pharmacological tests for determining their inhibitory effect on the MGL enzyme.

Tests comprised measuring the activity, in vitro, of the compounds of the invention on the MGL enzyme.

The inhibitory activity with respect to MGL is given by the concentration which inhibits 50% of the activity of MGL.

The inhibitory activity was measured in a radioenzymatic assay based on measuring the product of hydrolysis of 2-oleoyl glycerol ([³H] 2-OG) by MGL. The products of hydrolysis of [³H] 2-OG, labeled on the glycerol, are oleic acid and [³H]glycerol, and the source of MGL enzyme is a homogenate of mouse brain from which the cerebellum and the medulla oblongata have been removed. The mouse brains are removed, and stored at −80° C. until they are used or homogenized immediately for twice 5 seconds using a Precellys apparatus at 5000 rpm (Bertin) in a 10 mM tris-HCl, 150 mM NaCl, 1 mM EDTA buffer (pH 8) at 4° C. The concentration of the homogenates is then adjusted to 7.5 µg/µl.

The dilution series of the compounds is prepared from stock solutions at 20 mM in 100% DMSO. The first dilution of this series is prepared in 100% DMSO, then the second is prepared in the enzymatic reaction buffer (50 mM phosphate, 0.1% BSA) leading to the preparation of a 10-times concentrated concentration range. The test compounds are preincubated at the selected concentration for 20 minutes with the mouse brain homogenate preparation. The final concentration of DMSO in the enzymatic reaction does not exceed 0.1%.

Assaying of the MGL activity is carried out in a 96-well microplate in a final reaction volume of 100 µl. Briefly, 75 µg of proteins, preincubated with the test compounds, are diluted in 50 mM of phosphate buffer containing 0.1% of BSA and incubated, for 20 minutes at ambient temperature, in the presence of 50 µM of 2-OG containing an amount of [³H] 2-OG of 0.027 µCi/well (specific activity of 20 Ci/mmol). The reaction is stopped and the products formed are separated by adding and mixing 100 µl of chloroform/methanol (1/1). After stirring for 10 minutes, the microplate is centrifuged for 15 minutes at 4000 g and a 30 µl aliquot of the aqueous phase containing the [³H]glycerol produced is removed and then counted for 5 minutes by liquid scintillation (Wallac 1450 Microbeta).

Under these conditions, the most active compounds of the invention have an $IC_{50}$ (concentration which inhibits 50% of the control enzymatic activity of MGL) of between 0.001 and 0.1 µM.

For example, compounds No. 1 and 7 showed an $IC_{50}$ of 0.004 and 0.025 µM, respectively.

It therefore appears that the compounds according to the invention have an inhibitory activity with respect to MGL.

The compounds according to the invention can therefore be used for the preparation of medicaments, in particular of medicaments which inhibit the MGL enzyme.

Thus, according to another of its aspects, a subject of the invention is medicaments which comprise a compound of formula (I), or an addition salt of the latter with a pharmaceutically acceptable acid, or else a hydrate or a solvate of the compound of formula (I).

These medicaments find use in therapeutics, in particular in the treatment and prevention of:

pain, in particular acute or chronic pain of neurogenic type: migraine, neuropathic pain including forms associated with the herpes virus and with diabetes;

acute or chronic pain associated with inflammatory diseases: arthritis, rheumatoid arthritis, osteoarthritis, spondylitis, gout, vasculitis, Crohn's disease, irritable bowel syndrome;

acute or chronic peripheral pain;

dizziness, vomiting, nausea, in particular subsequent to chemotherapy;

eating disorders, in particular anorexia and cachexia of various natures;

metabolic syndrome and its manifestations, including obesity;

dyslipidemia and manifestations thereof, including atherosclerosis and coronary diseases;

neurological and psychiatric pathological conditions; shaking, dyskinesia, dystonia, spasticity, obsessive-compulsive behavior, Tourette's syndrome, all forms of depression and anxiety of any nature and origin, mood disorders, psychoses;

acute and chronic neurodegenerative diseases: Parkinson's disease, Alzheimer's disease, senile dementia, Huntington's chorea, lesions associated with cerebral ischaemia and with cranium and medullary trauma, amyotrophic lateral sclerosis;

epilepsy;

sleep disorders including sleep apnea;

cardiovascular diseases, in particular hypertension, cardiac arrhythmias, arteriosclerosis, heart attack, cardiac ischaemia;

renal ischaemia;

cancers: benign skin tumors, brain tumors and papillomas, prostate tumors, brain tumors (glioblastomas, medulloepitheliomas, medulloblastomas, neuroblastomas, tumors of embryonic origin, astrocytomas, astroblastomas, ependyomas, oligodendrogliomas, plexus tumors, neuroepitheliomas, epiphyseal tumors, ependymoblastomas, malignant meningiomas, sarcomatosis, malignant melanomas, schwannomas);

immune system disorders, in particular autoimmune diseases: psoriasis, lupus erythematosus, diseases of the connective tissue or collagen diseases, Sjögren's syndrome, ankylosing spondylarthritis, undifferentiated spondylarthritis, Behcet's disease, hemolytic autoimmune anemias, multiple sclerosis, amyotrophic lateral sclerosis, amyloses, transplant rejection, diseases affecting the plasmocytic line;

allergic diseases: immediate or delayed hypersensitivity, allergic rhinitis or conjunctivitis, contact dermatitis;

parasitic, viral or bacterial infectious diseases: AIDS, meningitis;

inflammatory diseases, in particular diseases of the joints: arthritis, rheumatoid arthritis, osteoarthritis, spondylitis, gout, vasculitis, Crohn's disease, irritable bowel syndrome;

osteoporosis;

ocular conditions: ocular hypertension, glaucoma;

pulmonary conditions: respiratory tract diseases, bronchospasms, coughing, asthma, chronic bronchitis, chronic respiratory tract obstruction, emphysemas;

gastrointestinal diseases: irritable bowel syndrome, intestinal inflammatory disorders, ulcers, diarrhea;

urinary incontinence and bladder inflammation.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt, a hydrate or a solvate of said compound, and also at least one pharmaceutically acceptable excipient. Said excipients are selected according to the pharmaceutical form and the method of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or a possible salt, solvate or hydrate thereof, can be administered in unit administration form, as a mixture with conventional pharmaceutical excipients, to animals and to human beings for the prophylaxis or treatment of the disorders or diseases above.

Suitable unit administration forms comprise oral forms such as tablets, soft or hard gel capsules, powders, granules and oral solutions or suspensions, sublingual, buccal, intratracheal, intraocular and intranasal administration forms, and forms for administration by inhalation, topical, transdermal, subcutaneous, intramuscular or intravenous administration forms, rectal administration forms, and implants. For topical application, the compounds according to the invention can be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Maize starch | 15.0 mg |
| Hydroxypropylmethylcellulose | 2.25 mg |
| Magnesium stearate | 3.0 mg |

According to another of its aspects, the present invention also relates to a method for treating the pathological conditions indicated above, which comprises the administration of an effective dose of a compound according to the invention, or a pharmaceutically acceptable salt or hydrate or solvate thereof, to a patient.

What is claimed is:

1. A compound of the formula (I):

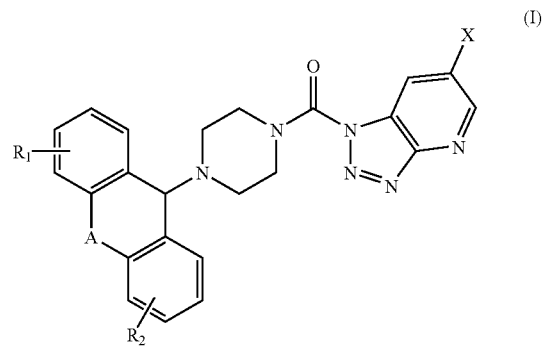

in which:

X is hydrogen, halogen, $(C_1\text{-}C_6)$alkyl, $(C_1\text{-}C_6)$alkoxy, halo $(C_1\text{-}C_6)$alkyl, $S(O)_m R''$, hydroxyl or cyano;

A is a bond, $(C_1\text{-}C_2)$alkylene or $(C_2)$alkenyl group;

or A is absent and the attachment is a benzhydryl group;

$R_1$ and $R_2$ are, independently of one another, one or more groups selected from the group consisting of hydrogen, $(C_1\text{-}C_6)$alkyl, $(C_1\text{-}C_6)$alkoxy, $(C_3\text{-}C_7)$cycloalkyl, $(C_3\text{-}C_7)$cycloalkyl$(C_1\text{-}C_6)$alkyl, $(C_3\text{-}C_7)$cycloalkyl$(C_1\text{-}C_6)$alkoxy, halogen, cyano, $C(O)R'$, $C(O)OR'$, $C(O)NR_{10}R_{20}$, $NO_2$, $NR_{10}R_{20}$ and $NR_{10}C(O)\text{—}R_{20}$ group, wherein $(C_1\text{-}C_6)$alkyl and $(C_1\text{-}C_6)$alkoxy are optionally substituted with one or more groups selected, independently of one another, from halogen, hydroxyl, amino and $NR_{10}R_{20}$;

R' is selected from hydrogen, $(C_1\text{-}C_6)$alkyl, $(C_3\text{-}C_7)$cycloalkyl and $(C_3\text{-}C_7)$cycloalkyl$(C_1\text{-}C_6)$alkyl;

R'' is selected from $(C_1\text{-}C_6)$alkyl, $(C_3\text{-}C_7)$cycloalkyl and $(C_3\text{-}C_7)$cycloalkyl$(C_1\text{-}C_6)$alkyl; and $R_{10}$ and $R_{20}$ are, independently of one another, selected from hydrogen, $(C_1\text{-}C_6)$alkyl, $(C_3\text{-}C_7)$cycloalkyl and $(C_3\text{-}C_7)$cycloalkyl$(C_1\text{-}C_6)$alkyl; or $R_{10}$ and $R_{20}$ form a saturated or partially unsaturated ring containing from 5 to 7 carbon atoms and optionally containing a heteroatom chosen from 0, N or $S(O)_m$; wherein m represents 0, 1 or 2; or a salt thereof.

2. The compound of formula (I) according to claim 1, wherein:

X is hydrogen or halogen; and

A is a bond, or ($C_1$-$C_2$)alkylene; or when A is absent the attachment is a benzhydryl group; or a salt thereof.

3. The compound of formula (I) according to claim 1, wherein:

X is hydrogen or halogen;

A is a bond or ($C_1$-$C_2$)alkylene; and $R_1$ and $R_2$ are, independently of one another, one or more groups selected from hydrogen, halogen, cyano or alkoxy; or a salt thereof.

4. The compound of formula (I) according to claim 1, wherein:

X is hydrogen or halogen;

A is a bond or ethylene; and $R_1$ and $R_2$ are, independently of one another, one or more groups selected from hydrogen or halogen; or a salt thereof.

5. The compound of formula (I) according to claim 1, wherein:

X is hydrogen or chlorine;

A is a bond or ethylene; and $R_1$ and $R_2$ are, independently of one another, one or more groups selected from hydrogen, fluorine or chlorine; or a salt thereof.

6. The compound of formula (I) according to claim 1, which is selected from the group consisting of:

(4-benzhydrylpiperazin-1-yl)[1,2,3]triazolo[4,5-b]pyridin-1-ylmethanone;

(4-benzhydrylpiperazin-1-yl)(6-chloro[1,2,3]triazolo[4,5-b]pyridin-1-yl)methanone;

{4-[bis(4-fluorophenyl)methyl]piperazin-1-yl}[1,2,3]triazolo[4,5-b]pyridin-1-ylmethanone;

{4-[bis(4-chlorophenyl)methyl]piperazin-1-yl}[1,2,3]triazolo[4,5-b]pyridin-1-ylmethanone;

{4-[bis(4-fluorophenyl)methyl]piperazin-1-yl} (6-chloro[1,2,3]triazolo[4,5-b]pyridin-1-yl)methanone;

{4-[bis(4-chlorophenyl)methyl]piperazin-1-yl} (6-chloro[1,2,3]triazolo[4,5-b]pyridin-1-yl)methanone;

[4-(10,11-dihydro-5H-dibenzo[a,d] cyclohepten-5-yl)piperazin-1-yl][1,2,3]triazolo[4,5-b]pyridin-1-ylmethanone; and

[4-(9H-fluoren-9-yl)piperazin-1-yl][1,2,3]triazolo[4,5-b]pyridin-1-ylmethanone.

7. A process for preparing the compound of formula (I) according to claim 1, comprising:

reacting a compound of formula (II):

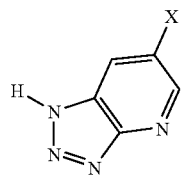

(II)

in which X is as defined in claim 1, with a compound of formula (III):

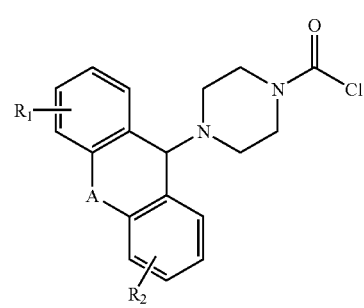

(III)

in which A, $R_1$ and $R_2$ are as defined in claim 1.

8. A process for preparing a compound of formula (I) according to claim 1, comprising:

reacting a compound of formula (IV):

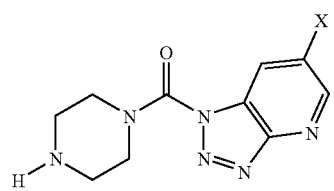

(IV)

in which X is as defined in claim 1, with a compound of formula (V):

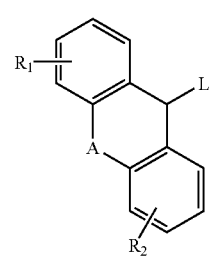

(V)

in which A, $R_1$ and $R_2$ are as defined in claim 1 and L represents a leaving group.

9. A compound of formula (IV):

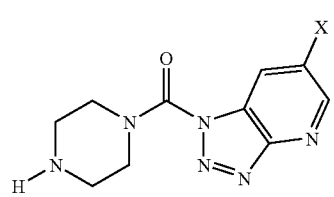

(IV)

in which

X is hydrogen, halogen, ($C_1$-$C_6$)alkyl, ($C_1$-$C_6$)alkoxy, halo($C_1$-$C_6$)alkyl, $S(O)_mR''$, hydroxyl or cyano.

10. A pharmaceutical composition comprising a compound of formula (I) according to claim 1 or a pharmaceutically acceptable salt thereof and at least one pharmaceutically acceptable excipient.

11. A pharmaceutical composition comprising a compound of formula (I) according to claim 2 or a pharmaceutically acceptable salt thereof and at least one pharmaceutically acceptable excipient.

12. A pharmaceutical composition comprising a compound of formula (I) according to claim 3 or a pharmaceutically acceptable salt thereof and at least one pharmaceutically acceptable excipient.

13. A pharmaceutical composition comprising a compound of formula (I) according to claim 4 or a pharmaceutically acceptable salt thereof and at least one pharmaceutically acceptable excipient.

14. A pharmaceutical composition comprising a compound of formula (I) according to claim 5 or a pharmaceutically acceptable salt thereof and at least one pharmaceutically acceptable excipient.

15. A pharmaceutical composition comprising a compound of formula (I) according to claim 6 or a pharmaceutically acceptable salt thereof and at least one pharmaceutically acceptable excipient.

* * * * *

UNITED STATES PATENT AND TRADEMARK OFFICE
CERTIFICATE OF CORRECTION

PATENT NO. : 7,868,007 B2  
APPLICATION NO. : 12/573961  
DATED : January 11, 2011  
INVENTOR(S) : Christian Hoornaert It is certified that error appears in the above-identified patent and that said Letters Patent is hereby corrected as shown below:

Title Page;  
On the first page, in field (56), in column 1, under "Other Publications", line 9, delete "1250" and insert -- 1260 --, therefor.

On the first page, in field (56), in column 1, under "Other Publications", line 16, delete "Monoacylglycerois" and insert -- Monoacylglycerols --, therefor.

In column 13, line 3, in claim 1, delete "0," and insert -- O, --, therefor.

Signed and Sealed this  
Thirteenth Day of September, 2011

David J. Kappos  
*Director of the United States Patent and Trademark Office*